United States Patent
Wang

(10) Patent No.: US 7,048,713 B2
(45) Date of Patent: May 23, 2006

(54) CATHETER HAVING AN IMPROVED BALLOON-TO-CATHETER BOND

(75) Inventor: Lixiao Wang, Long Lake, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/990,570

(22) Filed: Nov. 17, 2004

(65) Prior Publication Data

US 2005/0070846 A1 Mar. 31, 2005

Related U.S. Application Data

(63) Continuation of application No. 10/027,417, filed on Dec. 20, 2001, now Pat. No. 6,923,787.

(51) Int. Cl.
A61M 29/00 (2006.01)

(52) U.S. Cl. .............. 604/96.01; 604/103.06

(58) Field of Classification Search .......... 604/97.01, 604/164.01, 93.01, 103.06, 103.07, 103, 604/104, 196.01; 606/194, 191
See application file for complete search history.

(56) References Cited

U.S. PATENT DOCUMENTS

| | | | |
|---|---|---|---|
| 4,960,410 A | 10/1990 | Pinchuk | |
| 4,994,018 A | 2/1991 | Saper | |
| 5,047,045 A | 9/1991 | Arney et al. | |
| 5,063,018 A | 11/1991 | Fontirroche et al. | |
| 5,156,594 A | 10/1992 | Keith | |
| 5,176,698 A | 1/1993 | Burns et al. | |
| 5,195,969 A | 3/1993 | Wang et al. | |
| 5,304,134 A | 4/1994 | Kraus et al. | |
| 5,342,386 A | 8/1994 | Trotta | |
| 5,399,164 A | 3/1995 | Snoke et al. | |
| 5,425,712 A | 6/1995 | Goodin | |
| 5,499,973 A | 3/1996 | Saab | |
| 5,501,759 A | 3/1996 | Forman | |
| 5,512,051 A | 4/1996 | Wang et al. | |
| 5,533,985 A | 7/1996 | Wang | |
| 5,538,510 A | 7/1996 | Fontirroche et al. | |
| 5,554,121 A | 9/1996 | Ainsworth et al. | |
| 5,569,196 A | 10/1996 | Muni et al. | |
| 5,587,125 A | 12/1996 | Roychowdhury | |
| 5,603,991 A | 2/1997 | Kupiecki et al. | |
| 5,759,173 A | 6/1998 | Preissman et al. | |
| 5,759,191 A | 6/1998 | Barbere | |
| 5,769,819 A * | 6/1998 | Schwab et al. ............. 604/103 |
| 5,789,018 A | 8/1998 | Engelson et al. | |
| 5,820,594 A | 10/1998 | Fontirroche et al. | |
| 5,824,173 A | 10/1998 | Fontirroche et al. | |

(Continued)

FOREIGN PATENT DOCUMENTS

EP 0 453 960 A1 8/1993

(Continued)

Primary Examiner—Nicholas D. Lucchesi
Assistant Examiner—Laura A Bouchelle
(74) Attorney, Agent, or Firm—Crompton, Seager & Tufte, LLC

(57) ABSTRACT

A tie layer insert is disclosed to aid in bond formation between an expandable balloon and a distal portion of a catheter shaft. The tie layer insert can be a single layer applied directly to the structural surfaces, or alternatively, the tie layer may be incorporated into a preformed polymeric insert. In the latter embodiment, the polymeric insert may include several layers of polymeric material. During the manufacturing process, the preformed polymeric insert is positioned between the distal portion of the expandable balloon and the catheter shaft. The entire distal region is then processed to form a sealably bonded expandable balloon to the distal end of the catheter shaft.

16 Claims, 1 Drawing Sheet

U.S. PATENT DOCUMENTS

| | | | |
|---|---|---|---|
| 5,876,376 A * | 3/1999 | Schwab et al. | 604/103 |
| 5,902,631 A | 5/1999 | Wang et al. | |
| 6,010,521 A | 1/2000 | Lee et al. | |
| 6,020,071 A | 2/2000 | Watson | |
| 6,027,477 A | 2/2000 | Kastenhofer | |
| 6,086,556 A | 7/2000 | Hamilton et al. | |
| 6,106,889 A | 8/2000 | Beavers et al. | |
| 6,139,525 A | 10/2000 | Davis-Lemessy et al. | |
| 6,165,166 A | 12/2000 | Samuelson et al. | |
| 6,179,811 B1 | 1/2001 | Fugoso et al. | |
| 6,179,856 B1 | 1/2001 | Barbere | |
| 6,325,814 B1 | 12/2001 | Euteneuer et al. | |
| 6,375,637 B1 | 4/2002 | Campbell et al. | |
| 6,465,067 B1 | 10/2002 | Wang et al. | |
| 6,488,655 B1 | 12/2002 | Wantink et al. | |
| 6,491,619 B1 * | 12/2002 | Trauthen et al. | 600/3 |
| 6,530,938 B1 | 3/2003 | Lee et al. | |
| 6,547,768 B1 | 4/2003 | Trotta | |
| 6,638,245 B1 | 10/2003 | Miller et al. | |
| 6,706,010 B1 | 3/2004 | Miki et al. | |

FOREIGN PATENT DOCUMENTS

| | | |
|---|---|---|
| EP | 0 846 472 A1 | 6/1998 |

* cited by examiner

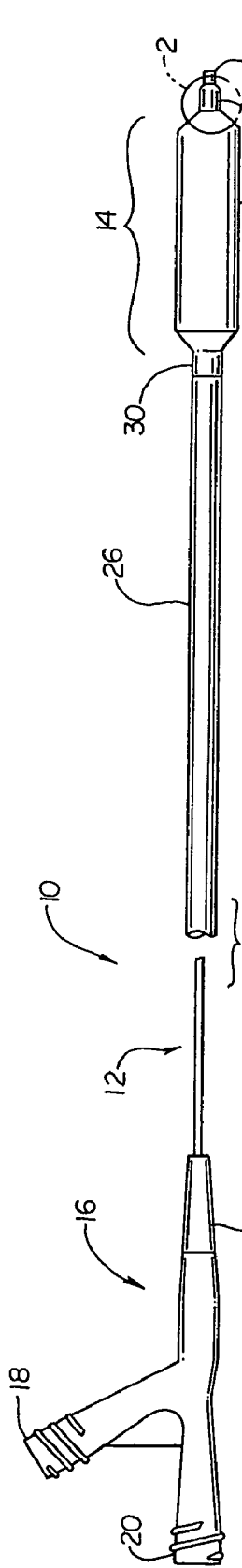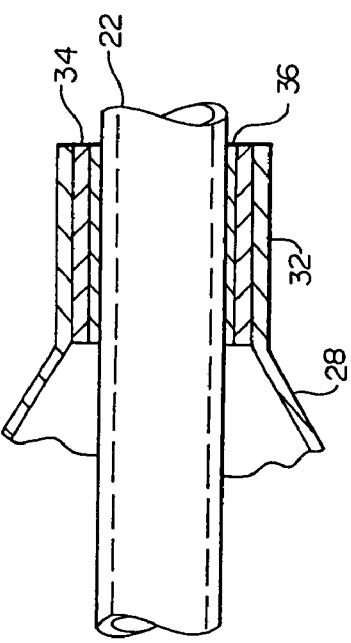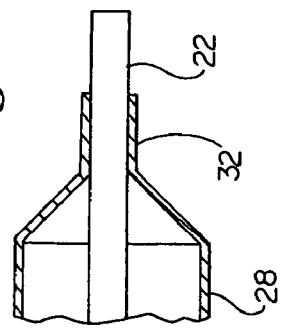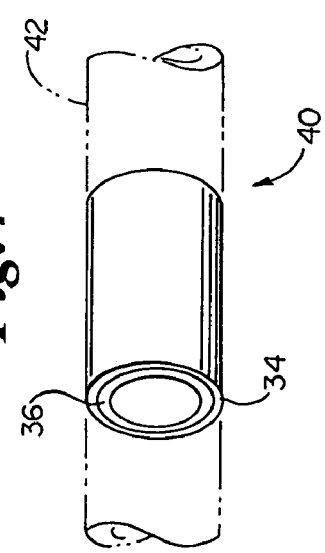

CATHETER HAVING AN IMPROVED BALLOON-TO-CATHETER BOND

CROSS-REFERENCE TO CO-PENDING APPLICATIONS

This application is a continuation of U.S. application Ser. No. 10/027,417, filed Dec. 20, 2001, now U.S. Pat. No. 6,923,787, the disclosure of which is incorporated herein by reference.

TECHNICAL FIELD

The present invention relates generally to the field of medical devices having an expandable balloon disposed proximate the distal portion of a shaft. More specifically, the present invention relates to improved physical properties, processing and performance of a bond formed between the waist of an expandable balloon and the portion of the tubular member of a catheter shaft to which it is bonded.

BACKGROUND OF THE INVENTION

Intravascular diseases are commonly treated by relatively non-invasive techniques such as percutaneous transluminal angioplasty (PTA) and percutaneous transluminal coronary angioplasty (PTCA). These therapeutic techniques are well known in the art and typically involve the use of a balloon catheter with a guidewire, possibly in combination with other intravascular devices such as stents. A typical balloon catheter has an elongate shaft with a balloon attached proximate the distal end and a manifold attached to the proximal end. In use, the balloon catheter is advanced over the guidewire such that the balloon is positioned adjacent a restriction in a diseased vessel. The balloon is then inflated and the restriction in the vessel is opened.

There are three basic types of intravascular catheters for use in such procedures including fixed-wire (FW) catheters, over-the-wire (OTW) catheters and single-operator-exchange (SOE) catheters. The general construction and use of FW, OTW and SOE catheters are all well known in the art. An example of an OTW catheter may be found in commonly assigned U.S. Pat. No. 5,047,045 to Arney et al. An example of an SOE balloon catheter is disclosed in commonly assigned U.S. Pat. No. 5,156,594 to Keith.

Manufacturers are constantly in search of materials and designs that enhance the performance of their intravascular catheters. One particular source of improvement has been the incorporation of performance enhancing polymeric materials into their intravascular catheter designs. Certain polymeric materials enable the catheter to be more lubricious, thereby aiding the advancement of a guidewire within the body of the catheter. Other polymeric materials make particular sections of the catheter more rigid, thereby aiding the catheter in its advancement through the patient's anatomy. The primary drawback to using specialized polymeric materials is that often the individual polymers forming the structural components are incompatible with one another. This is a particular problem for manufacturers who must combine the individual components to form a single operable intravascular catheter.

One solution to the use of incompatible polymers has been to place a layer between the two incompatible polymeric structural components that is sufficiently bondable to either component. In effect, this distinct layer "ties" the two structural components together, thereby receiving its commonly referred to name as a tie layer. Tie layers have been extruded over the length of intravascular catheters. This added layer, regardless of its thickness, affects the performance characteristics of an intravascular catheter shaft incorporating the tie layer.

Several performance characteristics that are important to intravascular catheters include pushability, trackability and crossability. Pushability refers to the catheter's ability to transmit force from the proximal end of the catheter to the distal end of the catheter. Trackability refers to the catheter's ability to navigate tortuous vasculature. Crossability refers to the catheter's ability to navigate the balloon catheter across narrow restrictions in the vasculature, such as stenosed vessels or fully and partially deployed stents. All of the above performance characteristics are interrelated and depend on the design of the catheter shaft over its length.

It is a manufacturing goal to reduce the profile of a manufactured intravascular catheter. A reduced profile catheter is less likely to positively engage the surrounding vascular walls. Additionally, a reduced profile catheter is also more likely to cross and re-cross over a stenosed region or a deployed stent.

SUMMARY OF THE INVENTION

The present invention maximizes the benefits of a tie layer in a balloon catheter by utilizing only a discrete length of tie layer where needed on the catheter. In particular to the present invention, a discrete length tie layer is disclosed to aid in bond formation between an expandable balloon and a distal portion of a catheter shaft. However, the discrete tie layer can be utilized at any bond on the catheter shaft where improved bonding is needed. The tie layer disclosed in the present invention can be a single layer applied directly to the structural surfaces, or alternatively, the tie layer may be incorporated into a preformed polymeric insert. In the latter embodiment, the polymeric insert may include several layers of polymeric material, each acting as or including the tie layer.

During the manufacturing process, the preformed polymeric insert is positioned around the outside surface of the catheter shaft proximate the distal end of the shaft, and a proximal or distal portion of a waist of the balloon overlays the preformed polymeric insert. The entire region is then processed to sealably bond the portion of the expandable balloon to the portion of the catheter shaft.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

FIG. 1 is a plan view of a balloon dilatation catheter in accordance with the present invention having a distal tip region;

FIG. 2 is an enlarged partial cross-sectional view of the distal tip region of the balloon dilatation catheter of FIG. 1;

FIG. 3 is an enlarged partial cross-sectional view of the area surrounding the distal balloon waist of the balloon dilatation catheter of FIG. 1; and FIG. 4 is perspective view of a cut away portion of tubular material depicting a series of coaxially disposed layers.

DETAILED DESCRIPTION OF THE PREFERRED EMBODIMENTS

The following detailed description should be read with reference to the drawings, in which like elements in different drawings are numbered identically. The drawings, which are not necessarily to scale, depict selected embodiments and are not intended to limit the scope of the invention. Examples of construction, materials, dimensions, and manufacturing processes are provided for selected elements.

Referring now to the drawings, FIG. 1 is a plan view of an over-the-wire (OTW) balloon catheter, which is representative of one type of catheter that can incorporate the present invention. Other intravascular catheter embodiments are additionally suitable without deviating from the spirit and scope of the present invention. For example, intravascular catheters suitable for incorporating the present invention also include fixed-wire (FW) catheters and single-operator-exchange (SOE) catheters.

The balloon catheter 10 includes a shaft assembly 12 and a balloon assembly 14 connected proximate the distal end of the shaft assembly 12. A conventional OTW-type manifold assembly 16 is connected to the proximal end of the shaft assembly 12. The proximal end of the shaft assembly 12 extends into the manifold assembly 16 and is bonded to the shaft assembly 12. Manifold ports 18 and 20 extend from the manifold assembly 16 for attaching and fluidly connecting ancillary apparatus to a lumen extending through the balloon catheter 10. Each manifold port includes a lumen terminating into either a common lumen or a dedicated lumen extending within the shaft assembly 12 (e.g., a guidewire lumen). Functionally, the manifold assembly 16 additionally provides a convenient place for a physician to apply longitudinal or rotational forces in order to manipulate the catheter 10 during a medical procedure.

Referring specifically to FIG. 1, the manifold assembly 16 illustrated includes two luer-type manifold ports 18 and 20. In alternative embodiments, the union between the manifold assembly 16 and ancillary medical devices (not shown) is completed using alternative connectors. A polymeric strain relief 24 can be snap-fit to the manifold assembly 16 in a preferred embodiment, and the shaft assembly 12 extends into the manifold assembly 16 through the strain relief 24.

In a preferred embodiment, the shaft assembly 12 comprises an outer tubular member 26 which is co-axially disposed about an inner tubular member 22 to define an annular inflation lumen therebetween over a substantial portion of the length of the catheter 10. Generally, the outer tubular member 26 in preferred embodiments has an outer diameter ranging from 0.040 inches to 0.045 inches with a wall thickness ranging from 0.0028 inches to 0.0044 inches. Materials used to form the outer tubular member 26 may vary to achieve the stiffness desired for the shaft assembly 12. Nylon and polyamides such as DURETHAN (available from Bayer) are particularly suitable for rigid outer tubular members. Other suitable materials for a rigid outer tubular member include polyetheretherketone (PEEK), polyimide (PI), and polyetherimide (PEI). Rigidity may additionally be imparted to the outer tubular member 26 by incorporating a braid on or within the tubular member. Polyether block amide (PEBA) is a relatively flexible polymeric material having a durometer of approximately 70D and could also be utilized for portions of the shaft assembly 12. Finally, the use of a polyamide such as CRISTAMID (available from Elf Atochem) imparts a slightly less rigid durometer than the rigid polyamides and slightly greater than the PEBA material, making it suitable for certain applications.

The inner tubular member 22 defines a guidewire lumen, which provides a passage for a guidewire (not shown). The inner tubular member 22 is generally made of polyethylene such as Marlex HDPE in preferred embodiments. In alternative embodiments, the inner tubular member 22 is made from or lined with a lubricious material such as polytetrafluoroethylene (PTFE). In one preferred embodiment, at the proximal end of the inner tubular member 22, the inner tubular member 22 has an outside diameter ranging from 0.024 inches to 0.026 inches, and most preferably about 0.025 inches. The inner diameter of the inner tubular member 22 preferably measures approximately 0.018 inches to 0.0195 inches, allowing for use of a 0.014-inch guidewire. The inner tubular member 22 has a wall thickness ranging from 0.0026 inches to 0.004 inches, and most preferably about 0.0032 inches. The outside diameter to wall thickness ratio must be sufficiently small to minimize the propensity for the shaft assembly 12, and more specifically, the inner tubular member 22 from kinking.

At the distal end of the shaft assembly 12 is a balloon assembly 14. The balloon assembly 14 includes an expandable balloon 28 having a proximal balloon waist 30 and a distal balloon waist 32. The proximal balloon waist 30 affixes the expandable balloon 28 to the outer tubular member 26 near its distal end by means of an adhesive, or alternatively, or in combination with, RF, laser or other thermal bonding. The distal balloon waist 32, as shown best in FIG. 2, similarly affixes the expandable balloon 28 to the inner tubular member 22 near its distal end by means of an adhesive bond and/or an RF, laser or other thermal bond. This particular balloon assembly 14 arrangement allows the expandable balloon 28 to be in fluid communication with the annular inflation lumen defined between the outer tubular member 26 and the inner tubular member 22. In preferred embodiments, a portion of the inner tubular member 22 extends distally beyond the distal balloon waist 32.

As described in detail above, the inner tubular member 22 is preferably made of a polyethylene material such as Marlex HDPE. The expandable balloon 28, on the other hand, is preferably made of a PEBA material such as PEBAX. These two materials are sufficiently dissimilar in chemical composition to affect the bonding between them. In particular, the dissimilarities between the two material compositions may affect certain thermal bonding procedures. As a result, the effectiveness of the bond between the two structural components having been formed from these certain thermal bonding procedures may be structurally compromised. Likewise, similar bonding effects may be seen if materials such as nylon, Hytrel, Arnitel or other polymers are selected as the balloon material.

Under certain circumstances, bonding failure may result in the separation of a portion of the distal balloon waist 32 from the inner tubular member 22. During a procedure, such separation may result in an inflation fluid leak when such fluid is supplied. The balloon dilation catheter 10 is deployed once the catheter is properly advanced and positioned across a targeted site within a patient's anatomy. When in position, inflation fluid is directed through the catheter's annular inflation lumen into the expandable balloon 28. As the pressure within the expandable balloon 28 increases, fluid trapped within the expandable balloon 28 causes the expandable balloon's inflation. A fissure in the bond sealing the distal balloon waist 32 to the inner tubular member 22 would result in a leak, thereby decreasing the inflation efficiency of the expandable balloon 28.

As with the distal balloon waist bond, bonding may be more difficult between the proximal balloon waist 30 and the portion of shaft to which it is affixed depending upon the selection of each polymeric material. The present invention is discussed in detail with respect to the distal waist bond, but is understood to be equally applicable to the proximal waist bond when dissimilar polymers are selected for the balloon and portion of the shaft to which the proximal waist is affixed.

With current manufacturing processes, the bonds formed between the distal balloon waist 32 and the inner tubular member 22 or proximal waist 30 and outer tubular member 26 are sufficiently strong to ensure a patient's safety during a medical procedure. The bonding between these two structural components, however, is a subject of constant improvement. Achieving the strongest bond possible when two dissimilar materials form their respective structural components is imperative to the success of the medical device and the safety of the patient. As such, an improved bond is desired to further curb the concerns of both practitioners and patients alike regarding the functionality and safety of catheters using this design.

Success in bonding the distal balloon waist 32 to the inner tubular member 22 or the proximal waist 30 to the outer tubular member 26 has been traditionally achieved using an adhesive. In these traditional methods, the adhesive is first applied between the two components. The two components are then bonded together to form the completed sealed union. There exist drawbacks, however, to using adhesives in such bonding procedures. For example, adhesives that are suitable for joining the two catheter components are commonly associated with long curing times, sensitivity to ambient conditions (including humidity and temperature), and the need for extensive surface treatment. As a result, bonding between the distal balloon waist 32 and the inner tubular member 22 and the proximal balloon waist 30 and outer tubular member 26 is typically time and labor intensive.

Adhesives common in catheter manufacturing also often take hours to cure. Moreover, procedures for bonding the balloon waist to the tubular member are highly dependent on operator skill. Assemblers must initially apply the appropriate amount of adhesive between the two catheter components to insure proper adhesion. In certain embodiments, the assembler may then sculpt a backfill onto the bond using additional adhesive to provide a smooth transition. Assembler errors and curing times may result in substantial delays. Delays in catheter production increase the manufacturer's costs.

The present invention identifies the use of a selected group of polymeric materials that aid in bonding the distal balloon waist 32 to the inner tubular member 22 or the proximal balloon waist 30 to the outer tubular member 26. In effect, the selected group of polymeric materials "ties" the two structural components having differing material compositions together. Therefore, hereinafter, the layer of polymeric material disposed between either the distal balloon waist 32 and the inner tubular member 22 or the proximal waist 30 and the outer tubular member 26 is called a tie layer.

Tie layers suitable for the present invention possess a bonding affinity to both materials forming the distal balloon waist 32 of the expandable balloon 28 and the inner tubular member 22. More specifically, in preferred embodiments, the tie layer material of the present invention is selected because it has a bonding affinity to polyethylene, PTFE, polyamide, PEBA, nylon, Hytrel, Arnitel or other suitable polymers used in a catheter's construction. The first two materials are preferred materials for forming the inner tubular member 22 and the latter materials are preferred materials for forming the distal balloon waist 32. Tie layer materials particularly suitable for the present invention include a linear low density polyethylene such as Plexar. The tie layer material may be heat-shrinkable and first heat shrunk to conform to the shaft, followed by bonding of the balloon waist. Alternative tie layer materials suitable for bonding materials forming the inner tubular member 22 to materials forming the distal balloon waist 32, being known in the art, are also incorporated as within the spirit and scope of the present invention.

Although the difficulty in bonding the distal balloon waist 32 to the inner tubular member 22 has been highlighted, other bonding areas along the catheter may be aided through tie layers. For example, a segment of tie layer may be placed between the proximal balloon waist 30 and the outer tubular member 26 to aid in bonding the expandable balloon 28 to the catheter shaft 12. As with the bonding between the distal balloon waist 32 and the inner tubular member 22, there may exist some bonding incompatibility between the materials comprising the proximal balloon waist 30 and the outer tubular member 26. A discrete section of tie layer material positioned between these two structural components may alleviate these bonding difficulties. Thus, the following sections discuss the bonding incompatibility between the distal balloon waist 32 and the inner tubular member 22 for illustrative purposes only, as other portions experiencing bonding difficulties may also be treated with the specific and precise placement of a tie layer.

Unlike traditional bonding procedures, discussed in detail above, a tie layer permits manufacturers to form a secured bond between the distal balloon waist 32 and the inner tubular member 22 using thermal bonding processing alone. Adhesives, although they may still be used, are not required to form a secure bond. Thus, the inclusion of a tie layer when attaching the balloon assembly to the catheter shaft may decrease consumer costs by reducing the errors and curing times associated with traditional bond processing procedures.

FIG. 3 shows an enlarged cross-sectional view of a distal tip region of a balloon dilation catheter 10 having a tie layer disposed therein. More specifically, two polymeric layers, a first layer 34 and a second layer 36, are shown disposed between the distal balloon waist 32 and the inner tubular member 22. Although two layers are specifically illustrated, a single tie layer is sufficient to form a sealably secure bond between the distal balloon waist 32 and the inner tubular member 22. Likewise, more than two tie layers may be disposed between the distal balloon waist 32 and the inner tubular member 22 in order to achieve a particular bonding and style configuration. Choosing the appropriate layer configuration often depends upon the specific materials utilized for the various structural components, as well as the desired shape for the distal tip of the catheter.

In certain embodiments, both the first layer 34 and the second layer 36 may comprise tie layer materials. For example, the first tie layer 34, because of its positioning, may possess a greater bonding affinity to materials forming a distal balloon waist 32. Whereas the second tie layer 36 may possess a greater bonding affinity to materials forming an inner tubular member 22. Although either the first 34 or the second 36 tie layer may possess a bonding affinity to both the distal balloon waist 32 and the inner tubular member 22, the layer distribution as described may provide the maximum bonding efficiency for the region as a whole.

Manufacturing a catheter distal tip in accordance with the present invention begins by first inserting a mandrel (not shown) into the distal end of the inner tubular member 22. The insertion of the mandrel insures against deformation of the catheter tip during the subsequent thermal processing events. Once the mandrel is inserted, the tie layers, preferably preformed as an insert, are disposed between the inner tubular member 22 and the distal balloon waist 32. In one embodiment, each tie layer is disposed over the inner tubular member 22, or alternatively, upon a preceding tie layer. The properly positioned tie layer is then thermally processed individually. In preferred embodiments, the tie layer insert is substantially the same length as the distal waist of the balloon, although it can be slightly longer or shorter and still provide adequate bonding. The short segment tie layer discrete to the balloon waist area provides a distinct advantage over the user of a tie layer over a greater length of the shaft in that the tie layer affects stiffness of the area in which it is used.

In an alternative embodiment, multiple individual tie layers are disposed between the inner tubular member 22 and the distal balloon waist 32. Once the individual tie layers are properly positioned, they are all then thermally processed together, forming an effective fluid tight seal in the distal tip region of the catheter 10.

In yet another embodiment, a single polymeric insert 40 comprising a plurality of tie layers is disposed between the inner tubular member 22 and the distal balloon waist 32. The tie layers within this polymeric insert 40 are thermally bonded during their extrusion process. In a preferred embodiment, the polymeric insert 40 is formed by extruding the plurality of tie layers into a tubular form. Multiple polymeric inserts 40 are then derived from the single tubular extrusion 42 by cutting the tubular extrusion 42 at appropriate increments. Further, the polymeric inserts may be sized to fit the shaft utilizing a necking process after extrusion.

FIG. 4 depicts a segment of the tubular extrusion 42 in phantom. Along the length of the tubular extrusion 42, a cut away portion of the tubular extrusion 42 is highlighted. This highlighted portion depicts a resulting polymeric insert 40 having a plurality of coaxially disposed tie layers 34 and 36. This polymeric insert 40 is then disposed between the inner tubular member 22 and the distal balloon waist 32. Once properly positioned, the distal balloon waist 32, the polymeric insert 40 and the inner tubular member 22 are thermally processed together to form a fluid tight seal in the distal tip region of a catheter 10.

Numerous characteristics and advantages of the invention covered by this document have been set forth in the foregoing description. It will be understood, however, that this disclosure is, in many respects, only illustrative. Changes may be made in details, particularly in matters of shape, size and ordering of steps without exceeding the scope of the invention. The invention's scope is, of course, defined in the language in which the appended claims are expressed.

What is claimed is:

1. A balloon catheter having a proximal end and a distal end, the catheter comprising:
   an inner tubular member extending along at least a distal portion of the catheter, the inner tubular member having a proximal end and a distal end;
   an outer tubular member disposed about the inner tubular member, the outer tubular member having a proximal end and a distal end, the inner tubular member extending distally beyond the distal end of the outer tubular member;
   a balloon having a proximal end and a distal end, the distal end of the balloon including a distal waist; and
   a discrete tubular insert formed with a tie material;
   wherein the balloon distal waist is secured onto the discrete tubular insert; and the discrete tubular insert is secured onto the inner tubular member such that the discrete tubular insert extends from a location distal the distal end of the outer tubular member to a location proximate the distal end of the catheter.

2. The balloon catheter of claim 1, wherein the discrete tubular insert ends proximal of the distal end of the catheter.

3. The balloon catheter of claim 1, wherein the discrete tubular insert comprises an inner layer of a first tie material suitable for securing to the inner tubular member and an outer layer of a second tie material suitable for securing to the balloon.

4. The balloon catheter of claim 3, wherein the inner tubular member is formed with polyethylene, and the balloon is formed with a polyether block amide.

5. The balloon catheter of claim 1, wherein the discrete tubular insert includes a linear low density polyethylene.

6. The balloon catheter of claim 1, wherein the inner tubular member is formed with polytetrafluoroethylene, and wherein the discrete tubular insert is formed with a tie material having a high affinity for polytetrafluoroethylene.

7. The balloon catheter of claim 1, wherein the discrete tubular insert is formed of multiple layers.

8. A balloon catheter having a proximal end and a distal end, the catheter comprising:
   an inner tubular member extending along at least a distal portion of the catheter, the inner tubular member having a proximal end and a distal end;
   an outer tubular member disposed about the inner tubular member, the outer tubular member having a proximal end and a distal end;
   a balloon having a proximal end and a distal end, the distal end of the balloon including a distal waist having a length; and
   a discrete tubular insert having a length approximating the length of the distal balloon waist;
   wherein the balloon distal waist is secured onto the discrete tubular insert, and the discrete tubular insert is secured onto the inner tubular member.

9. The balloon catheter of claim 8, wherein the discrete tubular insert comprises an inner layer of a first tie material suitable for securing to the inner tubular member and an outer layer of a second tie material suitable for securing to the balloon.

10. The balloon catheter of claim 9, wherein the inner tubular member is formed with polyethylene, and the balloon is formed with a polyether block amide.

11. The balloon catheter of claim 8, wherein the discrete tubular insert includes a linear law density polyethylene.

12. The balloon catheter of claim 8, wherein the inner tubular member is formed with polytetrafluoroethylene, and wherein the discrete tubular insert is formed with a tie material having a high affinity for polytetrafluoroethylene.

13. A balloon catheter having a proximal end and a distal end, the catheter comprising:
   an inner tubular member extending along at least a portion of the catheter, the inner tubular member having a proximal end and a distal end;
   an outer tubular member disposed about the inner tubular member, the outer tubular member having a proximal end and a distal end, wherein the inner tubular member extends distally beyond the distal end of the outer tubular member;

a balloon having a proximal end and a distal end, the distal end of the balloon including a distal waist having a length; and a polymeric tubular insert having a proximal end, a distal end, an inner surface and an outer surface, the polymeric tubular insert disposed between the inner tubular member and the distal waist of the balloon such that the proximal end of the polymeric tubular insert is distal the proximal end of the balloon and the distal end of the polymeric tubular insert is proximate the distal end of the balloon;

wherein the outer surface of the polymeric tubular insert is contiguous with and thermally bonded to an inner surface of the distal waist of the balloon and the inner surface of the polymeric tubular insert is contiguous with and thermally bonded to an outer surface of the inner tubular member.

14. The balloon catheter of claim 13, wherein the polymeric tubular insert has a length that is substantially the same as the length of the distal waist of the balloon.

15. The balloon catheter of claim 13, wherein the polymeric tubular insert includes a plurality of layers.

16. The balloon catheter of claim 13, wherein the distal end of the inner tubular member extends distal of the distal end of the balloon.

* * * * *

UNITED STATES PATENT AND TRADEMARK OFFICE
CERTIFICATE OF CORRECTION

| | | |
|---|---|---|
| PATENT NO. | : 7,048,713 B2 | Page 1 of 1 |
| APPLICATION NO. | : 10/990570 | |
| DATED | : May 23, 2006 | |
| INVENTOR(S) | : Wang | |

It is certified that error appears in the above-identified patent and that said Letters Patent is hereby corrected as shown below:

Column 8
Line 53, delete "law" and insert therefor: -- low --.

Signed and Sealed this

First Day of August, 2006

JON W. DUDAS
*Director of the United States Patent and Trademark Office*